(12) United States Patent
Johnson et al.

(10) Patent No.: US 12,178,905 B2
(45) Date of Patent: Dec. 31, 2024

(54) FLEECE FOR POUCHED PRODUCT WITH CONTROLLED BASIS WEIGHT

(71) Applicant: NICOVENTURES TRADING LIMITED, London (GB)

(72) Inventors: Savannah Johnson, Winston-Salem, NC (US); Ronald K. Hutchens, East Bend, NC (US); David Neil McClanahan, Winston-Salem, NC (US); Pankaj Patel, Clemmons, NC (US); Travis O'Neal, Pinnacle, NC (US); Dwayne William Beeson, Kernersville, NC (US); Wesley Steven Jones, Lexington, NC (US)

(73) Assignee: Nicoventures Trading Limited, London (GB)

( * ) Notice: Subject to any disclaimer, the term of this patent is extended or adjusted under 35 U.S.C. 154(b) by 1011 days.

(21) Appl. No.: 17/159,723

(22) Filed: Jan. 27, 2021

(65) Prior Publication Data

US 2021/0169791 A1  Jun. 10, 2021

Related U.S. Application Data

(63) Continuation of application No. PCT/IB2020/061595, filed on Dec. 7, 2020.
(Continued)

(51) Int. Cl.
*A61K 9/00* (2006.01)
*A24B 13/00* (2006.01)
(Continued)

(52) U.S. Cl.
CPC ............ *A61K 9/0056* (2013.01); *A24B 13/00* (2013.01); *A24B 15/16* (2013.01); *A61K 45/06* (2013.01);
(Continued)

(58) Field of Classification Search
CPC .... A61K 9/0056; A61K 45/06; A61K 31/465; A61K 9/006; A61K 31/00; A24B 13/00;
(Continued)

(56) References Cited

U.S. PATENT DOCUMENTS 2,475,241 A  7/1949 Hermanson
3,338,992 A  8/1967 Kinney
(Continued)

FOREIGN PATENT DOCUMENTS

EP  3192380  7/2017
GB  1273040  5/1972
(Continued)

OTHER PUBLICATIONS

Liu "Flavoring-Changing Chewing Gum" Science and Food UCLA, Jul. 7, 2015, pp. 1-5. https://scienceandfooducla.woodpress.com/2015/0/07/flavor-changing-chewing-gum/.
(Continued)

*Primary Examiner* — James C Yager
(74) *Attorney, Agent, or Firm* — Womble Bond Dickinson (US) LLP

(57) ABSTRACT

The disclosure provides oral pouched products including a fleece material with a controlled basis weight. In some embodiments, the oral pouched products may include a material within a porous pouch, wherein the porous pouch includes a fleece material having a basis weight of at least about 35 gsm. In some embodiments, the oral pouched products may include fleece materials have a thickness of at least about 0.2 mm or less than about 0.1 mm. In some embodiments, the pouched products may be configured for rapid or extended release of components contained therein or may be tailored to provide a desired release profile.

11 Claims, 1 Drawing Sheet

Related U.S. Application Data

(60) Provisional application No. 62/945,567, filed on Dec. 9, 2019.

(51) Int. Cl.
*A24B 15/16* (2020.01)
*A61K 45/06* (2006.01)
*A23L 27/00* (2016.01)
*A23L 33/105* (2016.01)
*A23L 33/15* (2016.01)
*A23L 33/175* (2016.01)
*A24F 23/02* (2006.01)
*D04H 1/58* (2012.01)

(52) U.S. Cl.
CPC .............. *A23L 27/72* (2016.08); *A23L 33/105* (2016.08); *A23L 33/15* (2016.08); *A23L 33/175* (2016.08); *A24F 23/02* (2013.01); *D04H 1/58* (2013.01); *Y10T 428/1307* (2015.01)

(58) Field of Classification Search
CPC ......... A24B 15/16; A24B 15/10; A23L 27/72; A23L 33/105; A23L 33/15; A23L 33/175; A23L 27/79; A23L 33/21; A24F 23/02; A23P 10/10; D04H 1/58; Y10T 428/1307
See application file for complete search history.

(56) References Cited

U.S. PATENT DOCUMENTS

| | | |
|---|---|---|
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,734,812 A | 5/1973 | Yazawa |
| 3,802,817 A | 4/1974 | Matsuki et al. |
| 3,849,241 A | 11/1974 | Buntin et al. |
| 3,972,759 A | 8/1976 | Buntin |
| 4,340,563 A | 7/1982 | Appel et al. |
| 4,622,259 A | 11/1986 | McAmish et al. |
| 4,907,605 A | 3/1990 | Ray et al. |
| 5,167,244 A | 12/1992 | Kjerstad |
| 5,200,246 A | 4/1993 | Sabee |
| 5,334,446 A | 8/1994 | Quantrille et al. |
| 7,032,601 B2 | 4/2006 | Atchley et al. |
| 7,498,281 B2 | 3/2009 | Iwasaki et al. |
| 7,861,728 B2 | 1/2011 | Holton, Jr. et al. |
| 7,950,399 B2 | 5/2011 | Winterson et al. |
| 7,980,251 B2 | 7/2011 | Winterson et al. |
| 8,067,046 B2 | 11/2011 | Schleef et al. |
| 8,124,147 B2 | 2/2012 | Cheng et al. |
| 8,336,557 B2 | 12/2012 | Kumar et al. |
| 8,557,071 B2 | 10/2013 | Weiler |
| 8,627,828 B2 | 1/2014 | Strickland et al. |
| 8,747,562 B2 | 6/2014 | Mishra et al. |
| 8,833,378 B2 | 9/2014 | Axelsson et al. |
| 8,846,075 B2 | 9/2014 | Jonsson et al. |
| 8,863,755 B2 | 10/2014 | Zhuang et al. |
| 8,931,493 B2 | 1/2015 | Sebastian et al. |
| 8,978,661 B2 | 3/2015 | Atchley et al. |
| 8,992,974 B2 | 3/2015 | McCarty |
| 9,061,824 B2 | 6/2015 | Torrence et al. |
| 9,066,540 B2 | 6/2015 | Atchley et al. |
| 9,125,434 B2 | 9/2015 | Fuisz |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,358,296 B2 | 6/2016 | McCarty |
| 9,402,414 B2 | 8/2016 | Griscik et al. |
| 9,402,809 B2 | 8/2016 | Axelsson et al. |
| 9,414,624 B2 | 8/2016 | Carroll et al. |
| 9,462,827 B2 | 10/2016 | Carroll et al. |
| 9,468,233 B2 | 10/2016 | Macko et al. |
| 9,521,864 B2 | 12/2016 | Gao et al. |
| 9,693,582 B2 | 7/2017 | Carroll et al. |
| 9,848,634 B2 | 12/2017 | Fuisz |
| 9,854,830 B2 | 1/2018 | Gao et al. |
| 9,854,831 B2 | 1/2018 | Gao et al. |
| 9,884,015 B2 | 2/2018 | Gao et al. |
| 9,925,145 B2 | 3/2018 | Hübinette et al. |
| 9,930,909 B2 | 4/2018 | Gao et al. |
| 9,986,756 B2 | 6/2018 | Gao et al. |
| 9,999,243 B2 | 6/2018 | Gao et al. |
| 10,105,320 B2 | 10/2018 | Gao et al. |
| 10,130,120 B2 | 11/2018 | Mishra et al. |
| 10,244,786 B2 | 4/2019 | Gao et al. |
| 10,258,076 B2 | 4/2019 | Carroll et al. |
| 10,315,889 B2 | 6/2019 | Kreischer et al. |
| 10,327,467 B2 | 6/2019 | Carroll et al. |
| 10,334,873 B2 | 7/2019 | Mishra et al. |
| 10,463,070 B2 | 11/2019 | Carroll et al. |
| 10,609,949 B2 | 4/2020 | Hodin et al. |
| 10,639,275 B2 | 5/2020 | Gao et al. |
| 10,647,459 B2 | 5/2020 | Persson |
| 2004/0094474 A1 | 5/2004 | Heinrich et al. |
| 2004/0118421 A1 | 6/2004 | Hodin et al. |
| 2004/0121689 A1 | 6/2004 | Anderson et al. |
| 2004/0166756 A1 | 8/2004 | Kurihara et al. |
| 2005/0061339 A1 | 3/2005 | Hansson et al. |
| 2007/0012328 A1 | 1/2007 | Winterson et al. |
| 2007/0062549 A1 | 3/2007 | Holton et al. |
| 2007/0186941 A1 | 8/2007 | Holton, Jr. et al. |
| 2007/0190157 A1 | 8/2007 | Sanghvi et al. |
| 2008/0029110 A1 | 2/2008 | Dube et al. |
| 2008/0085649 A1 | 4/2008 | Salamero et al. |
| 2008/0202532 A1 | 8/2008 | Wygal |
| 2008/0202536 A1 | 8/2008 | Torrence et al. |
| 2008/0249492 A1 | 10/2008 | Schmidt |
| 2008/0302682 A1 | 12/2008 | Engstrom et al. |
| 2008/0317911 A1 | 12/2008 | Schleef et al. |
| 2009/0022917 A1 | 1/2009 | Gedevanishvili et al. |
| 2009/0133704 A1 | 5/2009 | Strickland et al. |
| 2010/0018539 A1 | 1/2010 | Brinkley et al. |
| 2010/0018541 A1 | 1/2010 | Gerardi et al. |
| 2010/0330236 A1 | 12/2010 | Miyahara et al. |
| 2011/0180087 A1 | 7/2011 | Gee et al. |
| 2011/0268809 A1 | 11/2011 | Brinkley et al. |
| 2011/0303232 A1 | 12/2011 | Williams |
| 2011/0303511 A1 | 12/2011 | Brinkley et al. |
| 2012/0031416 A1 | 2/2012 | Atchley et al. |
| 2012/0051672 A1 | 3/2012 | Foss et al. |
| 2012/0055493 A1 | 3/2012 | Novak, III et al. |
| 2012/0103353 A1 | 5/2012 | Sebastian |
| 2012/0237640 A1 | 9/2012 | Buffet et al. |
| 2013/0206150 A1 | 8/2013 | Duggins et al. |
| 2013/0251779 A1 | 9/2013 | Svandal et al. |
| 2013/0276801 A1 | 10/2013 | Byrd et al. |
| 2014/0017286 A1 | 1/2014 | Nilsson |
| 2014/0026912 A1 | 1/2014 | Rushforth et al. |
| 2014/0083438 A1 | 3/2014 | Sebastian et al. |
| 2014/0141677 A1 | 5/2014 | Tai et al. |
| 2014/0157728 A1 | 6/2014 | Williams |
| 2014/0255452 A1 | 9/2014 | Reddick et al. |
| 2014/0271791 A1 | 9/2014 | Mishra et al. |
| 2015/0068545 A1 | 3/2015 | Moldoveanu et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0175329 A1 | 6/2015 | Wilke et al. |
| 2016/0000140 A1 | 1/2016 | Sebastian et al. |
| 2016/0073689 A1 | 3/2016 | Sebastian et al. |
| 2016/0157515 A1 | 6/2016 | Chapman et al. |
| 2016/0165953 A1 | 6/2016 | Goode, Jr. |
| 2016/0192703 A1 | 7/2016 | Sebastian et al. |
| 2016/0208440 A1 | 7/2016 | Byrd et al. |
| 2016/0324777 A1 | 11/2016 | Victor et al. |
| 2017/0188622 A1 | 7/2017 | Wilson |
| 2017/0280764 A1 | 10/2017 | Sahlén et al. |
| 2017/0318858 A1 | 11/2017 | Hodin et al. |
| 2018/0051002 A1 | 2/2018 | Dull et al. |
| 2018/0140007 A1 | 5/2018 | Aspgren et al. |

(56) References Cited

U.S. PATENT DOCUMENTS

| | | |
|---|---|---|
| 2018/0153211 A1 | 6/2018 | Persson |
| 2018/0255801 A1 | 9/2018 | Victor |
| 2018/0255826 A1 | 9/2018 | Persson et al. |
| 2019/0255035 A1 | 8/2019 | Bruun |
| 2019/0291900 A1 | 9/2019 | Persson et al. |
| 2020/0037638 A1 | 2/2020 | Faraci et al. |
| 2020/0128870 A1 | 4/2020 | Hassler et al. |
| 2020/0275689 A1 | 9/2020 | Lewerenz |
| 2020/0297024 A1 | 9/2020 | Bodin |
| 2020/0297026 A1 | 9/2020 | Kannisto et al. |
| 2020/0383372 A1 | 12/2020 | Stahl et al. |
| 2020/0383373 A1 | 12/2020 | Stahl et al. |
| 2021/0068446 A1 | 3/2021 | Keller et al. |
| 2021/0169790 A1 | 6/2021 | Johnson et al. |

FOREIGN PATENT DOCUMENTS

| | | | |
|---|---|---|---|
| GB | 2319265 | 5/1998 | |
| WO | WO 2007/037962 | 4/2007 | |
| WO | WO 2010/014506 | 2/2010 | |
| WO | WO-2010022360 A2 * | 2/2010 | ............ A24B 13/00 |
| WO | WO 2016/083463 | 6/2016 | |
| WO | WO 2019/036243 | 2/2019 | |
| WO | WO 2020/169514 | 8/2020 | |

OTHER PUBLICATIONS

Kiekins et al., "Non-Wovens From Cotton Fibres for Absorbent Products Obtained by the Needle-Punching Process," *AUTEX Research Journal*, Dec. 2002, 2(4), 9 pp.

Patel et al., "Needle Punching Technology," Department of Textile Engineering, The Maharaha Sayajirao University of Baroda, Vadodara, Feb. 2010, 9 pp.

Pinnau et al., "Formation and Modification of Polymeric Membranes: Overview," *Membrane Formation and Modification, ACS Symposium Series, American Chemical Society*. Washington, DC, 1999, 22 pp.

\* cited by examiner

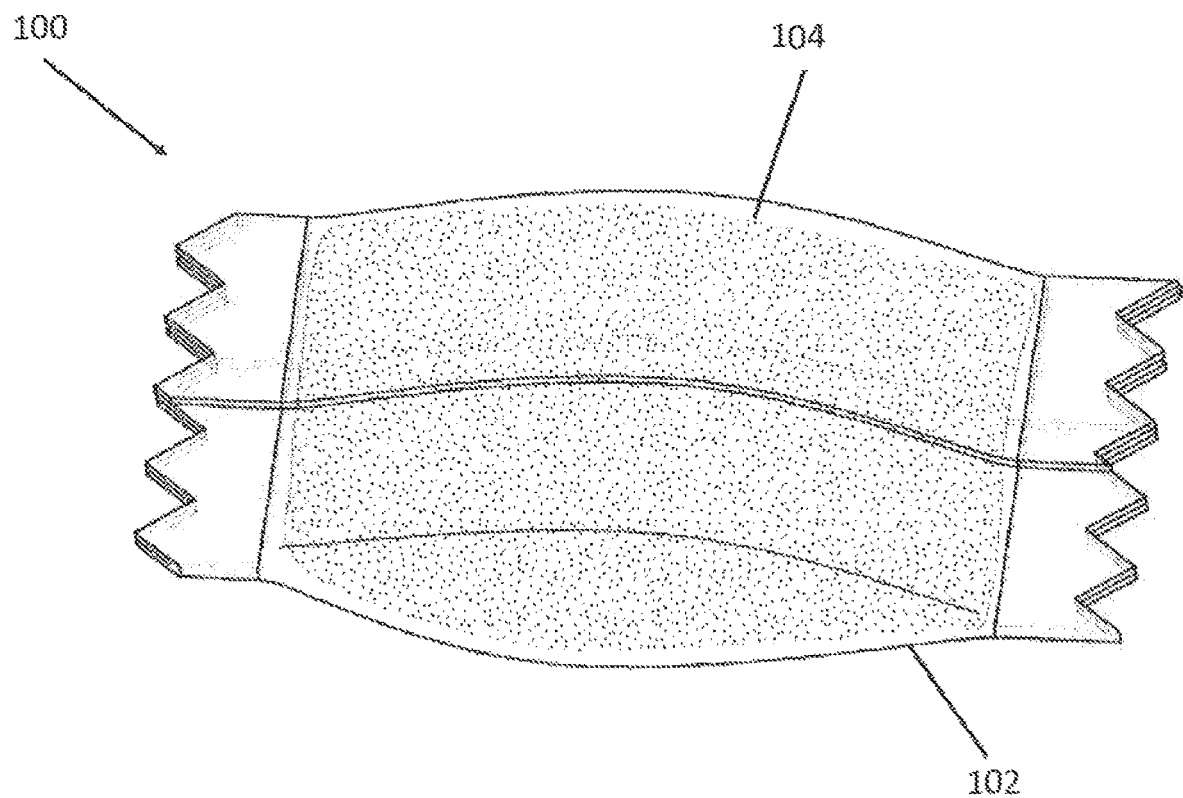

FLEECE FOR POUCHED PRODUCT WITH CONTROLLED BASIS WEIGHT

CROSS-REFERENCE TO RELATED APPLICATIONS

The present application is a continuation of International Application No. PCT/IB2020/061595, filed Dec. 7, 2020, and claims priority to and the benefit of U.S. Provisional App. No. 62/945,567, filed Dec. 9, 2019, both of which are incorporated herein by reference in their entirety.

FIELD OF THE DISCLOSURE

The present disclosure relates to flavored products intended for human use. The products are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

All-white snus portions are growing in popularity, and offer a discrete and aesthetically pleasing alternative to traditional snus. Such modern "white" pouched products may include a bleached tobacco or may be tobacco-free.

BRIEF SUMMARY

The present disclosure generally provides oral products, including, but not limited to all-white snus portions. The products may be configured to impart a taste when used orally and, additionally or alternatively, may deliver active ingredients to a consumer, such as nicotine. The products and methods of the present disclosure in particular relate to fleece materials with controlled parameters and oral pouched products formed therefrom.

Some aspects of the present disclosure provide for oral pouched products comprising a material within a porous pouch, wherein the porous pouch may comprise a fleece material having a basis weight of at least about 35 gsm. In some embodiments, the fleece material may have a basis weight of about 35 gsm to about 40 gsm. In some embodiments, the fleece material may have a thickness of at least about 0.2 mm. In some embodiments, the fleece material may have a thickness of less than about 0.1 mm. In some embodiments, the fleece material may have a density of at least about 5 g/cc. In some embodiments, the fleece material may have a density of less than about 3 g/cc.

In some embodiments, the fleece material may further comprise a binder. In some embodiments, the material comprises an active ingredient. In some embodiments, the active ingredient may be selected from the group consisting of a nicotine component, botanicals, nutraceuticals, stimulants, amino acids, vitamins, cannabinoids, cannabimimetics, terpenes, and combinations thereof. In some embodiments, the material may comprise one or more additives selected from the group consisting of a flavoring agent, a salt, a sweetener, a binding agent, water, a humectant, a gum, an organic acid, a buffering agent and/or a pH adjuster, a tobacco material, and combinations thereof. In some embodiments, the oral pouched product may be substantially free of a tobacco material.

In some embodiments, the present disclosure may provide oral pouched products comprising a material within a porous pouch, wherein the porous pouch comprises a fleece material having a thickness of at least about 0.2 mm. In some embodiments, the fleece material may further comprise a binder. In some embodiments, the material comprises an active ingredient. In some embodiments, the active ingredient may be selected from the group consisting of a nicotine component, botanicals, nutraceuticals, stimulants, amino acids, vitamins, cannabinoids, cannabimimetics, terpenes, and combinations thereof.

In some embodiments, less than about 25% of the active ingredient is released from the oral pouched product in the first 5 minutes upon insertion into the oral cavity of a user. In some embodiments, the material may comprise one or more additives selected from the group consisting of a flavoring agent, a salt, a sweetener, a binding agent, water, a humectant, a gum, an organic acid, a buffering agent and/or a pH adjuster, a tobacco material, and combinations thereof. In some embodiments, the oral pouched product may be substantially free of a tobacco material.

In some embodiments, the present disclosure may provide oral pouched products comprising a material within a porous pouch, wherein the porous pouch comprises a fleece material having a thickness of less than about 0.1 mm. In some embodiments, the fleece material may further comprise a binder. In some embodiments, the material comprises an active ingredient. In some embodiments, the active ingredient may be selected from the group consisting of a nicotine component, botanicals, nutraceuticals, stimulants, amino acids, vitamins, cannabinoids, cannabimimetics, terpenes, and combinations thereof.

In some embodiments, at least 75% of the active ingredient may be released from the oral pouched product in the first 5 minutes upon insertion into the oral cavity of a user. In some embodiments, the material may comprise one or more additives selected from the group consisting of a flavoring agent, a salt, a sweetener, a binding agent, water, a humectant, a gum, an organic acid, a buffering agent and/or a pH adjuster, a tobacco material, and combinations thereof. In some embodiments, the oral pouched product may be substantially free of a tobacco material.

Various methods are provided in the present disclosure that relate to altering the release profiles of one or more components from an oral pouched product by changing one or more parameter of the fleece materials forming those pouched products. In some embodiments, for example, a method of providing rapid release of an active ingredient in an oral pouched product is provided, the method comprising providing a fleece material with a basis weight in the range of about 20 gsm to about 40 gsm and a thickness of less than about 0.1 mm, forming a porous pouch from the fleece material, and inserting a material comprising an active ingredient within the porous pouch to provide a pouched product, wherein at least 75% of the active ingredient is released from the pouched product in the first 5 minutes after insertion into the oral cavity of a user. In some embodiments, the active ingredient may be selected from the group consisting of a nicotine component, botanicals, nutraceuticals, stimulants, amino acids, vitamins, cannabinoids, cannabimimetics, terpenes, and combinations thereof. In some embodiments, the material may further comprise one or more additives selected from the group consisting of a flavoring agent, a salt, a sweetener, a binding agent, water, a humectant, a gum, an organic acid, a buffering agent and/or a pH adjuster, a tobacco material, and combinations thereof.

In some embodiments, the present disclosure provides methods for providing extended release of a flavoring agent in an oral pouched product. For example, in some embodiments, the method may comprise providing a fleece material with a basis weight of at least about 35 gsm and a thickness of at least about 0.2 mm, forming a porous pouch from the fleece material, and inserting a material comprising a flavoring agent within the porous pouch to provide a pouched product, wherein less than about 25% of the flavoring agent is released from the pouched product in the first 5 minutes after insertion into the oral cavity of a user. In some embodiments, the material may further comprise one or more additives selected from the group consisting of an active ingredient, a salt, a sweetener, a binding agent, water, a humectant, a gum, an organic acid, a buffering agent and/or a pH adjuster, a tobacco material, and combinations thereof. In some embodiments, the active ingredient may be selected from the group consisting of a nicotine component, botanicals, nutraceuticals, stimulants, amino acids, vitamins, cannabinoids, cannabimimetics, terpenes, and combinations thereof.

In some embodiments, the present disclosure provides methods of tailoring the release profile of one or more components from an oral pouched product into the oral cavity of a user, for example, the method may comprise selecting a fleece material on the basis of its density and/or basis weight, forming a porous pouch from the fleece material, and inserting a material comprising a flavoring agent and/or active ingredient within the porous pouch to provide a pouched product.

The disclosure includes, without limitations, the following embodiments.

Embodiment 1: An oral pouched product, comprising a material within a porous pouch, wherein the porous pouch comprises a fleece material having a basis weight of at least about 35 gsm.

Embodiment 2: The oral pouched product of Embodiment 1, wherein the fleece material has a basis weight of about 35 gsm to about 40 gsm.

Embodiment 3: The oral pouched product of any of Embodiments 1-2, wherein the fleece material has a thickness of at least about 0.2 mm.

Embodiment 4: The oral pouched product of any of Embodiments 1-2, wherein the fleece material has a thickness of less than about 0.1 mm.

Embodiment 5: The oral pouched product of any of Embodiments 1-3, wherein the fleece material has a density of at least about 5 g/cc.

Embodiment 6: The oral pouched product of any of Embodiments 1-2 and 4, wherein the fleece material has a density of less than about 3 g/cc.

Embodiment 7: The oral pouched product of any of Embodiments 1-6, wherein the fleece material further comprises a binder.

Embodiment 8: The oral pouched product of any of Embodiments 1-7, wherein the material comprises an active ingredient.

Embodiment 9: The oral pouched product of any of Embodiments 1-8, wherein the active ingredient is selected from the group consisting of a nicotine component, botanicals, nutraceuticals, stimulants, amino acids, vitamins, cannabinoids, cannabimimetics, terpenes, and combinations thereof.

Embodiment 10: The oral pouched product of any of Embodiments 1-9, wherein the material comprises one or more additives selected from the group consisting of a flavoring agent, a salt, a sweetener, a binding agent, water, a humectant, a gum, an organic acid, a buffering agent and/or a pH adjuster, a tobacco material, and combinations thereof.

Embodiment 11: The oral pouched product of any of Embodiments 1-9, wherein the oral pouched product is substantially free of a tobacco material.

Embodiment 12: An oral pouched product, comprising a material within a porous pouch, wherein the porous pouch comprises a fleece material having a thickness of at least about 0.2 mm.

Embodiment 13: The oral pouched product of Embodiment 12, wherein the fleece material further comprises a binder.

Embodiment 14: The oral pouched product of any of Embodiments 12-13, wherein the material comprises an active ingredient.

Embodiment 15: The oral pouched product of any of Embodiments 12-14, wherein the active ingredient is selected from the group consisting of a nicotine component, botanicals, nutraceuticals, stimulants, amino acids, vitamins, cannabinoids, cannabimimetics, terpenes, and combinations thereof.

Embodiment 16: The oral pouched product of any of Embodiments 12-15, wherein less than about 25% of the active ingredient is released from the pouched product in the first 5 minutes upon insertion into the oral cavity of a user.

Embodiment 17: The oral pouched product of any of Embodiments 12-16, wherein the material comprises one or more additives selected from the group consisting of a flavoring agent, a salt, a sweetener, a binding agent, water, a humectant, a gum, an organic acid, a buffering agent and/or a pH adjuster, a tobacco material, and combinations thereof.

Embodiment 18: The oral pouched product of any of Embodiments 12-16, wherein the oral pouched product is substantially free of a tobacco material.

Embodiment 19: An oral pouched product, comprising a material within a porous pouch, wherein the porous pouch comprises a fleece material having a thickness of less than about 0.1 mm.

Embodiment 20: The oral pouched product of Embodiment 19, wherein the fleece material further comprises a binder.

Embodiment 21: The oral pouched product of any of Embodiments 19-20, wherein the material comprises an active ingredient.

Embodiment 22: The oral pouched product of any of Embodiments 19-21, wherein the active ingredient is selected from the group consisting of a nicotine component, botanicals, nutraceuticals, stimulants, amino acids, vitamins, cannabinoids, cannabimimetics, terpenes, and combinations thereof.

Embodiment 23: The oral pouched product of any of Embodiments 19-22, wherein at least 75% of the active ingredient is released from the pouched product in the first 5 minutes upon insertion into the oral cavity of a user.

Embodiment 24: The oral pouched product of any of Embodiments 19-23, wherein the material comprises one or more additives selected from the group consisting of a flavoring agent, a salt, a sweetener, a binding agent, water, a humectant, a gum, an organic acid, a buffering agent and/or a pH adjuster, a tobacco material, and combinations thereof.

Embodiment 25: The oral pouched product of any of Embodiments 19-23, wherein the oral pouched product is substantially free of a tobacco material.

Embodiment 26: A method of providing rapid release of an active ingredient in an oral pouched product, the method comprising: providing a fleece material with a basis weight in the range of about 20 gsm to about 40 gsm and a thickness of less than about 0.1 mm; forming a porous pouch from the fleece material; and inserting a material comprising an active ingredient within the porous pouch to provide a pouched product; wherein at least 75% of the active ingredient is released from the pouched product in the first 5 minutes after insertion into the oral cavity of a user.

Embodiment 27: The method of Embodiment 26, wherein the active ingredient is selected from the group consisting of a nicotine component, botanicals, nutraceuticals, stimulants, amino acids, vitamins, cannabinoids, cannabimimetics, terpenes, and combinations thereof.

Embodiment 28: The method of any of Embodiments 26-27, wherein the material further comprises one or more components selected from the group consisting of a flavoring agent, a salt, a sweetener, a binding agent, water, a humectant, a gum, an organic acid, a buffering agent and/or a pH adjuster, a tobacco material, and combinations thereof.

Embodiment 29: A method of providing extended release of a flavoring agent in an oral pouched product, the method comprising: providing a fleece material with a basis weight of at least about 35 gsm and a thickness of at least about 0.2 mm; forming a porous pouch from the fleece material; and inserting a material comprising a flavoring agent within the porous pouch to provide a pouched product; wherein less than about 25% of the flavoring agent is released from the pouched product in the first 5 minutes after insertion into the oral cavity of a user.

Embodiment 30: The method of Embodiment 29, wherein the material further comprises one or more additives selected from the group consisting of an active ingredient, a salt, a sweetener, a binding agent, water, a humectant, a gum, an organic acid, a buffering agent and/or a pH adjuster, a tobacco material, and combinations thereof.

Embodiment 31: The method of any of Embodiments 29-30, wherein the active ingredient is selected from the group consisting of a nicotine component, botanicals, nutraceuticals, stimulants, amino acids, vitamins, cannabinoids, cannabimimetics, terpenes, and combinations thereof.

Embodiment 32: A method of tailoring the release profile of components from an oral pouched product into the oral cavity of a user comprising: selecting a fleece material on the basis of its density and/or basis weight; forming a porous pouch from the fleece material; and inserting a material comprising a flavoring agent and/or active ingredient within the porous pouch to provide a pouched product.

Embodiment 33: Use of a fleece material having a basis weight of at least about 35 gsm in an oral pouched product.

Embodiment 34: Use of a fleece material having a thickness of at least about 0.2 mm in an oral pouched product.

Embodiment 35: Use of a fleece material having a thickness of less than about 0.1 mm in an oral pouched product.

Embodiment 36: Use of a fleece material having a basis weight of at least 35 about gsm and a density of at least about 5 g/cc in an oral pouched product.

Embodiment 37: Use of a fleece material having a basis weight of at least about 35 gsm and a density of less than about 3 g/cc in an oral pouched product.

Embodiment 38: An oral pouched product having rapid release of an active ingredient therefrom, the oral product comprising a fleece material having a thickness of less than about 0.1 mm and an active, wherein at least about 75% of the active ingredient is released from the pouched product in the first 5 minutes after insertion into the oral cavity of a user.

Embodiment 39: An oral pouched product having extended release of a flavoring agent therefrom, the oral product comprising a fleece material having a basis weight of at least about 35 gsm and a thickness of at least about 0.2 mm and a flavoring agent, wherein less than about 25% of the flavoring agent is released from the pouched product in the first 5 minutes after insertion into the oral cavity of a user.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWING

Having thus described aspects of the disclosure in the foregoing general terms, reference will now be made to the accompanying drawing, which is not necessarily drawn to scale. The drawing is exemplary only, and should not be construed as limiting the disclosure.

FIG. 1 is a front perspective view illustrating a pouched product configured for oral use according to an example embodiment of the present disclosure.

DETAILED DESCRIPTION

The present disclosure provides fleece materials and products formed therefrom, the fleece materials and products particularly being configured for oral use. The basis weight of the fleece materials as described herein, and the caliper ("thickness") and density associated therewith, may be varied so as to effectively control the organoleptic properties (e.g., texture, mouth feel, and/or the release profile of components therefrom) of pouched products formed from these fleece materials. The products described herein may comprise fleece materials that are in the form of a water-permeable pouch material that surrounds a composition/mixture, also referred to herein as a "material" (e.g., a composition comprising one or more active ingredients and one or more additional components), and such pouched products may be adapted to or configured to provide for controlled release of the one or more components within the material, such as when in contact with the oral cavity of the user of the product.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the mixture including water. Unless otherwise indicated, reference to "weight percent" of a mixture reflects the total wet weight of the mixture (i.e., including water).

Pouched Products Configured for Oral Use

The disclosure generally provides pouch products configured for oral use. The term "configured for oral use" as used herein means that the product is provided in a form such that during use, saliva in the mouth of the user causes one or more of the components of the mixture (e.g., flavoring agents and/or nicotine) to pass into the mouth of the user. In certain embodiments, the product is adapted to deliver components to a user through mucous membranes in the user's mouth and, in some instances, said component is an active ingredient (including, but not limited to, for example, nicotine) that can be absorbed through the mucous membranes in the mouth when the product is used.

In particular, the disclosure provides products in the form of a material (generally a mixture of one or more components, sometimes referred to as a "substrate material"), disposed within a moisture-permeable container (e.g., a water-permeable pouch). Such mixtures in the water-permeable pouch format are typically used by placing a pouch containing the mixture in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the mixture therein (e.g., flavoring agents and/or nicotine) to pass through e.g., the water-permeable pouch and provide the user with flavor and satisfaction, and the user is not required to spit out any portion of the mixture. After about 10 minutes to about 60 minutes, typically about 15 minutes to about 45 minutes, of use/enjoyment, substantial amounts of the mixture have been absorbed through oral mucosa of the human subject, and the pouch may be removed from the mouth of the consumer for disposal.

Certain embodiments of the disclosure will be described with reference to FIG. 1, and these described embodiments involve snus-type products having an outer pouch and containing a mixture of components (as referenced herein below). The pouched product 100 includes a moisture-permeable container in the form of a porous pouch 102, which contains a material 104 comprising a mixture of components. As explained in greater detail below, such embodiments are provided by way of example only. In particular, the size and shape of the illustrated outer pouches can vary as described in detail herein. The mixture/construction of such packets or pouches, such as the porous pouch 102 in the embodiment illustrated in the figures, may be varied.

Suitable materials for the packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The mixture may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the mixture readily diffuse through the pouch and into the mouth of the user. Non-limiting examples of pouches are set forth in, for example, U.S. Pat. No. 5,167,244 to Kjerstad and U.S. Pat. No. 8,931,493 to Sebastian et al.; as well as US Patent App. Pub. Nos. 2016/0000140 to Sebastian et al.; 2016/0073689 to Sebastian et al.; 2016/0157515 to Chapman et al.; and 2016/0192703 to Sebastian et al., each of which are incorporated herein by reference. As provided herein, such example pouches are considered herein to be "conventional" products, which are provided as comparisons to the pouches disclosed herein, which exhibit various modifications with respect to one or more such conventional products. Pouches can be provided as individual pouches, or a plurality of pouches (e.g., 2, 4, 5, 10, 12, 15, 20, 25 or 30 pouches) that can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Generally, the pouched products include a material, which may be in the form of a powdered or granular composition adapted for oral use (e.g., a tobacco-containing composition, a nicotine-containing pharmaceutical composition, and/or a non-tobacco composition) that is disposed within a moisture-permeable container. That is, the composition adapted for oral use can be contained within a container, such as a pouch or bag, such as the type commonly used for the manufacture of snus types of products (e.g., a sealed, moisture permeable pouch that is sometimes referred to as a "portion"). A representative moisture permeable pouch can preferably be composed of a "fleece" type of material. For example, various fleece materials as described herein, e.g., such as fleece materials with a controlled basis weight that exhibit particular dissolution and/or organoleptic properties as described herein below. The orientation, size, and type of pouch material and the type and nature of the material contained therein are not construed as limiting thereof.

Embodiments of the present disclosure provide for pouched products comprising a fleece material, wherein the fleece material may be in the form of a fleece fabric material, such as in the form of a woven or nonwoven fabric comprising a plurality of fibers. In some embodiments, the fleece fabric material may be configured to have improved characteristics with respect to organoleptic properties and dissolution profile. For example, some embodiments provide for a product configured for oral use, the product comprising a fleece material in the form of a porous pouch, wherein the fleece material has a controlled basis weight. By controlling the basis weight of the fleece material the thickness and/or density of the fleece material may also be affected or altered. Fleece materials according to the present disclosure may be defined herein below with respect to their "basis weight," "density," and/or "thickness." Such terms are meant to be understood according to their typical meanings in the context of production of textile and nonwoven materials generally. Various combinations of such parameters may be varied in order to provide fleece materials and oral products produced therefrom, with varying organoleptic properties and/or dissolution profiles.

The present disclosure provides fleece materials with controlled basis weight and products that can include such fleece materials, optionally in combination with a material that may comprise one or more other additives or components therein. In such embodiments, the product may comprise a unitizing structure wherein the fleece material is in the form of a pouch that contains a material, such as in the form of a traditional pouched product or the like.

Fleece Material

As referenced above, the pouched products provided herein comprise at least one fleece material. "Fleece materials" as referred to herein may be in the form of a fleece fabric material, such as in the form of a woven or nonwoven fabric comprising a plurality of fibers.

As used herein, the term "fiber" is defined as a basic element of textiles. Fibers are often in the form of a rope- or string-like element. As used herein, the term "fiber" is intended to include fibers, filaments, continuous filaments, staple fibers, and the like.

The term "nonwoven" is used herein in reference to fibrous materials, webs, mats, batts, or sheets in which fibers are aligned in an undefined or random orientation. The nonwoven fibers are initially presented as unbound fibers or filaments. An important step in the manufacturing of nonwovens involves binding the various fibers or filaments together. The manner in which the fibers or filaments are bound can vary, and include thermal, mechanical and chemical techniques that are selected in part based on the desired characteristics of the final product, as discussed in more detail herein below.

In some embodiments, fleece materials of the present disclosure may be configured to have improved characteristics with respect to organoleptic properties and/or dissolution profile. A "fleece material" according to the present disclosure may be formed from various types of fibers (e.g., conventional cellulosic fibers (e.g., such as viscose fibers, regenerated cellulose fibers, cellulose fibers, and wood pulps), cotton fibers, wool fibers, other natural fibers, polymer/synthetic-type fibers, and combinations thereof) capable of being formed into a traditional fleece fabrics or other traditional pouch materials. For example, fleece materials may be provided in the form of a woven or nonwoven fabric. Suitable types of fleece materials, for example, are described in U.S. Pat. No. 8,931,493 to Sebastian et al.; US Patent App. Pub. No. 2016/0000140 to Sebastian et al.; and US Patent App. Pub. No. 2016/0073689 to Sebastian et al.; which are all incorporated herein by reference. Nonwoven fabric forming methods for natural and synthetic fibers may include drylaid, airlaid and wetlaid methods. In some embodiments, the nonwoven fabric can be formed using a spunlaid or spunmelt process, which includes both spunbond and meltblown processes, wherein such processes are understood to typically entail melting, extruding, collecting and bonding thermoplastic polymer materials to form a fibrous nonwoven web. The technique of meltblowing is known in the art and is discussed in various patents, for example, U.S. Pat. No. 3,849,241 to Butin, U.S. Pat. No. 3,987,185 to Buntin et al., U.S. Pat. No. 3,972,759 to Buntin, and U.S. Pat. No. 4,622,259 to McAmish et al., each of which is herein incorporated by reference in its entirety. General spunbonding processes are described, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and 30 U.S. Pat. No. 3,542,615 to Dobo et al., which are all incorporated herein by reference. In some embodiments, the types of fibers incorporated within fleece materials in the disclosed pouches may provide some benefit to the pouch (e.g., enhanced biodegradability, enhanced mouthfeel, etc.), while not significantly negatively impacting other characteristics of the fleece (e.g., taste, strength, mouthfeel, etc.).

In some embodiments, the fibers within the fleece material may include, but are not limited to, a polymer selected from the group consisting of a polymer selected from the group consisting of polyglycolic acid, polylactic acid, polyhydroxyalkanoates, polycaprolactone, polybutylene succinate, polybutylene succinate adipate, and copolymers thereof. In some embodiments, the fibers within the fleece material may be selected from the groups consisting of cellulose fibers, viscose fibers, regenerated cellulose fibers, other wood fibers, and the like.

The fleece materials can have varying basis weights, densities, thicknesses, porosities and other parameters as discussed below. For example, the fleece material can be formed such that the fiber orientation and porosity of the pouched product formed therefrom can retain the composition adapted for oral use that is enclosed within the outer water-permeable pouch, but can also allow the flavors of the composition to permeate through the fleece material to the user's oral cavity to be enjoyed by the consumer.

In some embodiments, the fleece material may comprise one or more binders. In some embodiments, the binder may comprise a heat sealable binder coating or a binder material (e.g., a coating or other additive) that may be added to the fibers prior to, during, or after forming the fleece material. As used herein, "heat sealable binder coatings" refers to coating materials, such as acrylic polymer compositions, applied to a substrate (e.g., a nonwoven web or fleece material) and which are capable of sealing seams of individual pouches upon heating. In some embodiments, a binder material can be added to the web fibers before or during the laying of the fibrous web (i.e., before the fibrous web is bonded to form a fleece material). In certain embodiments, a binder material can be added to the fleece material after it has been formed. In various embodiments, the binder material is in the form of a liquid coating. In certain embodiments, a binding powder can be applied to the fleece material. For example, powdered polyethylene can be used as a binder material. The liquid or powder coating can be applied, for example, between layers of fibers when cross-laying, air laying, or as an after treatment. A short exposure in an oven is sufficient to melt and fuse the binder material. It should be noted that application of a binder coating or a binder material to the fleece material generally increases the basis weight, thickness, and/or density of the fleece material.

Basis Weight/Density/Thickness

As noted above, the basis weight of the fleece materials, and the caliper ("thickness") and density associated therewith, may be varied so as to effectively control the organoleptic properties and dissolution profiles of oral products formed from these fleece materials. In some embodiments, fleece materials as described herein can have a basis weight of about 20 gsm to about 35 gsm, or about 25 gsm to about 30 gsm. Basis weight of a fabric can be measured using ASTM D3776/D3776M-09a(2013) (Standard Test Methods for Mass Per Unit Area (Weight) of Fabric), for example. In some embodiments, fleece materials as described herein may be provided in the form of a "high basis weight" fleece material.

As used herein, "high basis weight" refers to a fleece material having a basis weight of at least about 35 grams per square meter ("gsm"). For example, in some embodiments, a high basis weight fleece material may have a basis weight in the range of about 35 gsm to about 40 gsm, or, in some embodiments, may have a basis weight of at least about 35 gsm, at least about 36 gsm, at least about 37 gsm, at least about 38 gsm, at least about 39 gsm, or at least about 40 gsm. It should be noted that fleece materials manufactured at higher basis weights are generally characterized as being stiff and/or non-flexible in nature and thus, high basis weight fleece materials have not historically been used in the production of pouched products. However, products according the present disclosure advantageously can exhibit enhanced organoleptic properties when incorporating high basis weight fleece materials in the form of a porous pouch.

In some embodiments, fleece materials as described herein may be provided in the form of a "high thickness" fleece material or a "low thickness" fleece material. The thickness of a fleece material tends to be directly correlated with its basis weight. For example, as the basis weight of the fleece material is increased, in some embodiments, the thickness of the fleece materials may also increase. However, in some embodiments, the thickness of a fleece material may be altered without changing the basis weight of that fleece material by any method known in the art. For example, methods such as pressing and/or calendaring may be used to decrease the thickness of the fleece materials while maintaining the desired basis weight. In addition, the thickness of fleece materials having the same basis weight may be altered based on the production method and/or fiber input. In some embodiments, fleece materials manufactured from different types of fibers as described herein above may inherently have different thicknesses based on the specific properties of the fibers from which the fleece is formed. For example, a fleece material comprising fibers having a higher thickness and/or density may exhibit a lower thickness (e.g., as a result of using less fibers) when compared to a fleece material comprising fibers having a lower thickness and/or density, when both fleece materials have the same basis weight.

As used herein, "high thickness" refers to a fleece material having a thickness of at least about 0.2 mm. For example, in some embodiments, a high thickness fleece material may have a thickness in the range of about 0.2 mm to about 0.3 mm, or, in some embodiments, may have a thickness of at least about 0.2 mm, at least about 0.22 mm, at least about 0.24 mm, at least about 0.26 mm, at least about 0.28 mm, or at least about 0.30 mm. Such values may, in some embodiments, be limited by a maximum value (e.g., a maximum thickness through which saliva can pass in a reasonable period of time). Thickness of textile fabrics can be measured using ASTM D1777-96(2015) (Standard Test Method for Thickness of Textile Materials), for example.

As used herein, "low thickness" refers to a fleece material having a thickness of less than about 0.1 mm. For example, in some embodiments, a low thickness fleece material may have a thickness in the range of about 0.01 mm to about 0.1 mm, or in some embodiments, may have a thickness of less than about 0.1 mm, less than about 0.08 mm, less than about 0.06 mm, less than about 0.04 mm, or less than about 0.02 mm. Such values may, in some embodiments, be limited by a minimum value (e.g., a minimum thickness to ensure sufficient enclosure of the material inside and/or to prevent the material from passing too quickly therethrough).

In some embodiments, products comprising high basis weight fleece materials may further be provided in the form of a "high density" fleece material or a "low density" fleece material. Density of fleece materials may sometime be referred to as the "bulk" of the fleece material and both "density" and "bulk" are meant to be interchangeable as referenced herein. The density of a fleece material may be calculated, for example, using the basis weight and the thickness of the fleece material (e.g., Bulk=Thickness/Basis Weight). Thus, fleece materials having high basis weights can be provided in the form of a low density fleece material by reducing the thickness or in the form of a high density fleece material by increasing the thickness.

As used herein, "high density" refers to a fleece material having a density of at least about 5 grams per cubic centimeter ("g/cc"). For example, in some embodiments, a high density fleece material may have a density in the range of about 4 g/cc to about 8 g/cc, or, in some embodiments, may have a density of at least about 4 g/cc, at least about 4.5 g/cc, at least about 5.0 g/cc, at least about 5.5 g/cc, at least about 6.0 g/cc, at least about 6.5 g/cc, at least about 7.0 g/cc or at least about 7.5 g/cc. Such values may, in some embodiments, be limited by a maximum value (e.g., a maximum density through which saliva can pass in a reasonable period of time).

As used herein, "low density" refers to a fleece material having a density of at less than about 3 g/cc. For example, in some embodiments, a low density fleece material may have a density in the range of about 1 g/cc to about 4 g/cc, or, in some embodiments, may have a density of less than about 4 g/cc, less than about 3.5 g/cc, less than about 3.0 g/cc, less than about 2.5 g/cc, less than about 2.0 g/cc, or less than about 1.5 g/cc. Such values may, in some embodiments, be limited by a minimum value (e.g., a minimum density to ensure sufficient enclosure of the material inside and/or to prevent the material from passing too quickly therethrough).

Fleece materials according to the present disclosure may also be defined by various other measurements, for example, elongation, breaking strength, Tensile Energy Absorption (TEA), and/or porosity. In some embodiments, the fleece materials can have an elongation (e.g., the elongation at break when a peak load is applied) of about 70% to about 80%, e.g., about 78% and a peak load of about 4 lbs. to about 8 lbs., e.g., about 5.5 lbs. Elongation and breaking strength of textile fabrics can be measured using ASTM D5034-09 (2013) (Standard Test Method for Breaking Strength and Elongation of Textile Fabrics (Grab Test)), for example. In some embodiments, the fleece materials can have a TEA of about 35 to about 40, e.g., about 37 and a porosity of greater than about 10,000 ml/min/cm$^2$. TEA can be measured, for example, as the work done to break the specimen under tensile loading per lateral area of the specimen. Porosity, or air permeability of textile fabrics can be measured using ASTM D737-04(2012) (Standard Test method for Air Permeability of Textile Fabrics), for example.

Organoleptic Properties and Release Profile

Combinations of basis weights, thicknesses, and densities of fleece materials in the pouched products according to the present disclosure may vary. Advantageously, such combinations may be varied based on the desired release profile and organoleptic characteristics of the final product. For example, representative pouched products, including fleece materials with various combinations of these parameters, may include, but are not limited to, a "high basis weight" fleece material, a "high thickness" fleece material, a "low thickness" fleece material, a "high basis weight-high thickness" fleece material, a "high basis weight-low thickness" fleece material, a "high basis weight-high density" fleece material, or a "high basis weight-low density" fleece material. The listed examples are not to be construed as limiting and any combination of parameters (e.g., basis weight/thickness/density) within any of the disclosed ranges for those parameters may be altered in the fleece materials so as to provide the desired release profile and/or organoleptic properties in the final pouched product.

In some embodiments the oral products described herein may be configured to exhibit certain organoleptic properties when inserted into the mouth of a user of that product. Such properties may include, but are not limited to, softness, stiffness, firmness, hardness, stickiness, fluffiness, durability, chewability, workability, and the like. For example, in some embodiments, pouched products formed of fleece materials having a high basis weight and/or high thickness may provide increased durability (e.g., the ability to hold together when chewed or worked within the mouth of a user) when compared to pouched products having lower basis weights. In such embodiments, aggressive users are provided with an improved product that can be chewed or worked in the mouth of that user without falling apart and releasing the contents of the material contained therein into the mouth of the user. In some embodiments, pouched products formed of fleece materials having a high basis weight and/or high thickness may be softer in mouth feel when compared to common pouched products, e.g., such as pouched products comprising fleece materials with lower basis weights and/or thicknesses. In some embodiments, high basis weight fleece materials may also be used in pouched products that contain a material that is susceptible to discoloration of the porous pouch material. In such embodiments, the overall thickness and density of the high basis weight and high thickness fleece materials tend to minimize the discoloration effect caused by the material contained therein.

In some embodiments, the basis weight and the thickness of the fleece materials incorporated into the pouched products described herein may be varied to alter the dissolution or release profile of one or more components from the material. As discussed herein, various components may be included in the materials that are incorporated into the products comprising fleece materials described herein. For example, combinations of flavoring agents and/or active ingredients may be incorporated into the pouched products disclosed herein and the release profile of such ingredients therefrom can be controlled by altering various parameters with the fleece material (e.g., such as basis weight, thickness, density) used within those pouched products. "Release profile" as referred to herein is meant to define the amount of time it takes to deliver one or more components within the material to a user through mucous membranes in the user's mouth, for example, in some instances said ingredients (including, but not limited to, for example, nicotine) can be absorbed directly through the mucous membranes in the mouth when the product is used. For example, as described herein below, various configurations of the products disclosed herein may provide for the active ingredient to be delivered to a user of the product in a relatively short period of time (e.g., "rapid release") upon insertion of the product in the oral cavity, or the active ingredient may be released more slowly over time during use of the product by the user (e.g., "delayed release"). In some embodiments, the presence of both an active ingredient configured for rapid release and an active ingredient configured for delayed release in the product may provide for an "extended" release product that releases the active ingredients therein continuously over the life of the product. Generally, the amount of time required for a substantial amount of the one or more components to be absorbed directly through the mucous membranes in the mouth of the user may be in the range of about 1 minute to about 60 minutes, about 5 minutes to about 45 minutes, or about 10 minutes to about 30 minutes after insertion of the pouched product into the oral cavity of a user.

Pouched products according to the present disclosure may be adapted to or configured to provide a desired release profile in relation to one or more components (e.g., a flavoring agent, an active ingredient, etc. . . . ) by altering one or more of the basis weight, density, and thickness of the fleece material in the form of a porous pouch. For example, pouched products comprising a low thickness fleece material may be configured for rapid release of one or more active ingredients and/or one or more flavoring agents contained within the material. In some embodiments, pouched products comprising a low thickness fleece material may be configured such that at least 75% of the active ingredient and/or the flavoring agent may be released within the first 5 minutes after insertion of the pouched product into the oral cavity of a user. Without intending to be bound by theory, it should be noted that low thickness fleece materials exhibit much higher porosity therein, thus allowing for this rapid release of active ingredients and/or flavoring agents from products formed therefrom.

In some embodiments, pouched products comprising a high basis weight and/or a high thickness may be configured for delayed or extended release of one or more active ingredients and/or flavoring agents contained within the material therein. For example, in some embodiments, pouched products comprising a high basis weight and a high thickness may be configured such that at least 25% of the active ingredient and/or the flavoring agent may be released within the first 5 minutes after insertion of the pouched product into the oral cavity of a user. Without intending to be bound by theory, it should be noted that the thicker/denser fleece material may exhibit a much lower porosity and thus retain the active ingredient and/or the flavoring agent therein for a time such that release of the active ingredient and/or the flavoring agent therefrom is delayed. Advantageously, in some embodiments, products comprising high basis weight and/or high thickness fleece materials may be more easily impregnated with one or more active ingredients and/or flavoring agents when compared to other pouched products not comprising a high basis weight and high thickness fleece material.

The foregoing discussion provides non-limiting examples of configurations that can provide for desired release profiles, including one or more of: fast release or rapid release; slow release or extended release; delayed release; and the like. The release profile may be at least partially controlled by any one or more of the chemical nature of the active ingredient, the physical state of the active ingredient in the composition/product, a carrier/filler with which the active ingredient is combined (e.g., absorbed or adsorbed thereon), and solubility of the active ingredient. The percentages described with regard to the release rates noted above are referred to as being by weight based on the total weight of the oral composition.

Material within the Pouch

As noted above, pouched products generally comprise, in addition to the pouch-based exterior, a material within the pouch that typically comprises one or more active ingredients and/or one or more flavorants, and various other optional ingredients. The composition of the material within the pouches provided herein is not particularly limited, and can comprise any filling composition, including those included within conventional pouched products. Such compositions are generally mixtures of two or more components and as such, the compositions are, in some cases, referenced herein below as "mixtures." Certain components that can advantageously be included in the mixtures within certain embodiments of the pouched products provided herein are outlined generally below; however, it is to be understood that the discussion below is not intended to be limiting of the components that can be incorporated within the disclosed pouched products.

Active Ingredient

The material or composition as disclosed herein includes one or more active ingredients. As used herein, an "active ingredient" refers to one or more substances belonging to any of the following categories: API (active pharmaceutical ingredient), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods." These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, nicotine components, and/or pharmaceutical, nutraceutical, and medicinal ingredients (e.g., vitamins, such as A, B3, B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular product.

In certain embodiments, the active ingredient is selected from the group consisting of caffeine, taurine, GABA, theanine, vitamin C, lemon balm extract, ginseng, citicoline, sunflower lecithin, and combinations thereof. For example, the active ingredient can include a combination of caffeine, theanine, and optionally ginseng. In another embodiment, the active ingredient includes a combination of theanine, gamma-amino butyric acid (GABA), and lemon balm extract. In a further embodiment, the active ingredient includes theanine, theanine and tryptophan, or theanine and one or more B vitamins (e.g., vitamin B6 or B12). In a still further embodiment, the active ingredient includes a combination of caffeine, taurine, and vitamin C.

The particular percentages of active ingredients present will vary depending upon the desired characteristics of the particular product. Typically, an active ingredient or combination thereof is present in a total concentration of at least about 0.001% by weight of the material, such as in a range from about 0.001% to about 20%. In some embodiments, the active ingredient or combination of active ingredients is present in a concentration from about 0.1% w/w to about 10% by weight, such as, e.g., from about 0.5% w/w to about 10%, from about 1% to about 10%, from about 1% to about 5% by weight, based on the total weight of the material. In some embodiments, the active ingredient or combination of active ingredients is present in a concentration of from about 0.001%, about 0.01%, about 0.1%, or about 1%, up to about 20% by weight, such as, e.g., from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the material. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). In some embodiments, the compositions as disclosed herein can be characterized as free of any tobacco material (e.g., any embodiment as disclosed herein may be completely or substantially free of any tobacco material). By "substantially free" is meant that no tobacco material has been intentionally added. For example, certain embodiments can be characterized as having less than 0.001% by weight of tobacco, or less than 0.0001%, or even 0% by weight of tobacco.

When present, a botanical is typically at a concentration of from about 0.01% w/w to about 10% by weight, such as, e.g., from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the material.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include ashwagandha, *Bacopa monniera*, baobab, basil, *Centella asiatica*, Chai-hu, chamomile, cherry blossom, chlorophyll, cinnamon, citrus, cloves, cocoa, cordyceps, curcumin, damiana, *Dorstenia arifolia, Dorstenia odorata*, essential oils, eucalyptus, fennel, *Galphimia glauca*, ginger, *Ginkgo biloba*, ginseng (e.g., *Panax ginseng*), green tea, *Griffonia simplicifolia*, guarana, cannabis, hemp, hops, jasmine, *Kaempferia parviflora* (Thai ginseng), kava, lavender, lemon balm, lemongrass, licorice, lutein, maca, matcha, Nardostachys chinensis, oil-based extract of *Viola odorata*, peppermint, quercetin, resveratrol, *Rhizoma gastrodiae, Rhodiola,* rooibos, rose essential oil, rosemary, *Sceletium tortuosum*, Schisandra, Skullcap, spearmint extract, Spikenard, terpenes, tisanes, turmeric, *Turnera aphrodisiaca*, valerian, white mulberry, and *Yerba mate*.

In some embodiments, the active ingredient comprises lemon balm. Lemon balm (*Melissa officinalis*) is a mildly lemon-scented herb from the same family as mint (Lamiaceae). The herb is native to Europe, North Africa, and West Asia. The tea of lemon balm, as well as the essential oil and the extract, are used in traditional and alternative medicine. In some embodiments, the active ingredient comprises lemon balm extract. In some embodiments, the lemon balm extract is present in an amount of from about 1 to about 4% by weight, based on the total weight of the material.

In some embodiments, the active ingredient comprises ginseng. Ginseng is the root of plants of the genus *Panax*, which are characterized by the presence of unique steroid saponin phytochemicals (ginsenosides) and gintonin. Ginseng finds use as a dietary supplement in energy drinks or herbal teas, and in traditional medicine. Cultivated species include Korean ginseng (*P. ginseng*), South China ginseng (*P. notoginseng*), and American ginseng (*P. quinquefolius*). American ginseng and Korean ginseng vary in the type and quantity of various ginsenosides present. In some embodiments, the ginseng is American ginseng or Korean ginseng. In specific embodiments, the active ingredient comprises Korean ginseng. In some embodiments, ginseng is present in an amount of from about 0.4 to about 0.6% by weight, based on the total weight of the material.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the material. In some embodiments, the composition comprises caffeine in an amount of from about 1.5 to about 6% by weight, based on the total weight of the material;

Amino Acids

In some embodiments, the active ingredient comprises an amino acid. As used herein, the term "amino acid" refers to an organic compound that contains amine ($-NH_2$) and carboxyl ($-COOH$) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine. In some embodiments, the active ingredient comprises theanine. In some embodiments, the active ingredient comprises GABA. In some embodiments, the active ingredient comprises a combination of theanine and GABA. In some embodiments, the active ingredient is a combination of theanine, GABA, and lemon balm. In some embodiments, the active ingredient is a combination of caffeine, theanine, and ginseng. In some embodiments, the active ingredient comprises taurine. In some embodiments, the active ingredient is a combination of caffeine and taurine.

When present, an amino acid or combination of amino acids (e.g., theanine, GABA, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the material.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C. In some embodiments, the active ingredient is a combination of vitamin C, caffeine, and taurine.

When present, a vitamin or combination of vitamins (e.g., vitamin B6, vitamin B12, vitamin E, vitamin C, or a combination thereof) is typically at a concentration of from about 0.01% w/w to about 6% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, about 1%, about 2%, about 3%, about 4%, about 5%, or about 6% by weight, based on the total weight of the material.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, *Yerba mate, Yerba santa, Bacopa monniera, Withania somnifera*, Lion's mane, and silybum marianum. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12 (2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the material.

Nicotine Component

In certain embodiments, the active ingredient comprises a nicotine component. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the material, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the material. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the material.

In some embodiments, the products or compositions of the disclosure can be characterized as free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

In some embodiments, the active ingredient comprises a nicotine component (e.g., any product or composition of the disclosure, in addition to comprising any active ingredient or combination of active ingredients as disclosed herein, may further comprise a nicotine component).

Cannabinoids

In some embodiments, the active ingredient comprises one or more cannabinoids. As used herein, the term "cannabinoid" refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in cannabis; and synthetic cannabinoids, manufactured artificially. Cannabinoids found in cannabis include, without limitation: cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), and tetrahydrocannabivarinic acid (THCV A). In certain embodiments, the cannabinoid is selected from tetrahydrocannabinol (THC), the primary psychoactive compound in cannabis, and cannabidiol (CBD) another major constituent of the plant, but which is devoid of psychoactivity. All of the above compounds can be used in the form of an isolate from plant material or synthetically derived.

Alternatively, the active ingredient can be a cannabimimetic, which is a class of compounds derived from plants other than cannabis that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids.

When present, a cannabinoid (e.g., CBD) or cannabimimetic is typically in a concentration of at least about 0.1% by weight of the material, such as in a range from about 0.1% to about 30%, such as, e.g., from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the material.

Terpenes

Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl)propanoic acid), phosphatidylserine, myoinositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine. In some embodiments, the active ingredient comprises citicoline. In some embodiments, the active ingredient is a combination of citicoline, caffeine, theanine, and ginseng. In some embodiments, the active ingredient comprises sunflower lecithin. In some embodiments, the active ingredient is a combination of sunflower lecithin, caffeine, theanine, and ginseng.

The amount of API may vary. For example, when present, an API is typically at a concentration of from about 0.001% w/w to about 10% by weight, such as, e.g., from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the material.

In some embodiments, the composition is substantially free of any API. By "substantially free of any API" means that the composition does not contain, and specifically excludes, the presence of any API as defined herein, such as any Food and Drug Administration (FDA) approved therapeutic agent intended to treat any medical condition.

Flavoring Agent

In some embodiments, the material or composition comprises a flavoring agent. As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. In some embodiments, the material may include a single flavoring agent or a plurality of flavoring agents. If desired, one or more flavoring agents may be embedded within the fleece material, absorbed in or adsorbed on at least one surface of the fleece material, or impregnated within the fleece material.

Non-limiting examples of flavoring agents can include vanilla, coffee, chocolate/cocoa, cream, mint, spearmint, menthol, peppermint, wintergreen, eucalyptus, lavender, cardamon, nutmeg, cinnamon, clove, cascarilla, sandalwood, honey, jasmine, ginger, anise, sage, licorice, lemon, orange, apple, peach, lime, cherry, strawberry, terpenes, trigeminal sensates, and any combinations thereof. See also, Leffingwell et al., Tobacco Flavoring for Smoking Products, R. J. Reynolds Tobacco Company (1972), which is incorporated herein by reference. Flavorings also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The flavoring agent may be a volatile flavor component. As used herein, "volatile" refers to a chemical substance that forms a vapor readily at ambient temperatures (i.e., a chemical substance that has a high vapor pressure at a given temperature relative to a nonvolatile substance). Typically, a volatile flavor component has a molecular weight below about 400 Da, and often include at least one carbon-carbon double bond, carbon-oxygen double bond, or both. In one embodiment, the at least one volatile flavor component comprises one or more alcohols, aldehydes, aromatic hydrocarbons, ketones, esters, terpenes, terpenoids, or a combination thereof. Non-limiting examples of aldehydes include vanillin, ethyl vanillin, p-anisaldehyde, hexanal, furfural, isovaleraldehyde, cuminaldehyde, benzaldehyde, and citronellal. Non-limiting examples of ketones include 1-hydroxy-2-propanone and 2-hydroxy-3-methyl-2-cyclopentenone-1-one. Non-limiting examples of esters include allyl hexanoate, ethyl heptanoate, ethyl hexanoate, isoamyl acetate, and 3-methylbutyl acetate. Non-limiting examples of terpenes include sabinene, limonene, gamma-terpinene, beta-farnesene, nerolidol, thuj one, myrcene, geraniol, nerol, citronellol, linalool, and eucalyptol. In one embodiment, the at least one volatile flavor component comprises one or more of ethyl vanillin, cinnamaldehyde, sabinene, limonene, gamma-terpinene, beta-farnesene, or citral. In one embodiment, the at least one volatile flavor component comprises ethyl vanillin.

Filler

The material or composition as described herein may include at least one particulate filler component. Such particulate fillers may fulfill multiple functions, such as enhancing certain organoleptic properties such as texture and mouthfeel, enhancing cohesiveness or compressibility of the product, and the like. Generally, the fillers are porous particulate materials and are cellulose-based. For example, suitable particulate fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential particulate fillers include maltodextrin, dextrose, calcium carbonate, calcium phosphate, lactose, mannitol, xylitol, and sorbitol. Combinations of fillers can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the mixture based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "genetically modified" starches. Other starches are obtained and subsequently modified by chemical, enzymatic, or physical means. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, acetylation, hydroxypropylation, and/or partial hydrolysis. Enzymatic treatment includes subjecting native starches to enzyme isolates or concentrates, microbial enzymes, and/or enzymes native to plant materials, e.g., amylase present in corn kernels to modify corn starch. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, starch sodium octenyl succinate.

In some embodiments, the particulate filler component is a cellulose material or cellulose derivative. One particularly suitable particulate filler component for use in the products described herein is microcrystalline cellulose ("MCC"). The MCC may be synthetic or semi-synthetic, or it may be obtained entirely from natural celluloses. The MCC may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. In one embodiment, the mixture comprises MCC as the particulate filler component. The quantity of MCC present in the mixture as described herein may vary according to the desired properties.

The amount of particulate filler can vary, but is typically up to about 75 percent of the material by weight, based on the total weight of the material. A typical range of particulate filler (e.g., MCC) within the material can be from about 10 to about 75 percent by total weight of the mixture, for example, from about 10, about 15, about 20, about 25, or about 30, to about 35, about 40, about 45, or about 50 weight percent (e.g., about 20 to about 50 weight percent or about 25 to about 45 weight percent). In certain embodiments, the amount of particulate filler is at least about 10 percent by weight, such as at least about 20 percent, or at least about 25 percent, or at least about 30 percent, or at least about 35 percent, or at least about 40 percent, based on the total weight of the material.

In one embodiment, the particulate filler further comprises a cellulose derivative or a combination of such derivatives. In some embodiments, the mixture comprises from about 1 to about 10% of the cellulose derivative by weight, based on the total weight of the mixture, with certain embodiments comprising about 1 to about 5% by weight of cellulose derivative. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). In one embodiment, the cellulose derivative is one or more of methylcellulose, HPC, HPMC, hydroxyethyl cellulose, and CMC. In one embodiment, the cellulose derivative is HPC. In some embodiments, the mixture comprises from about 1 to about 3% HPC by weight, based on the total weight of the material.

Tobacco Material

In some embodiments, the material or composition of the pouched product may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a mixture as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The material disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the material most preferably includes tobacco lamina, or a tobacco lamina and stem mixture (of which at least a portion is smoke-treated). Portions of the tobaccos within the material may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the material optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral products, it is typical for a harvested plant of the *Nicotiana* species to be subjected to a curing process. The tobacco materials incorporated within the material for inclusion within products as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

Typical inclusion ranges for tobacco materials can vary depending on the nature and type of the tobacco material, and the intended effect on the final mixture, with an example range of up to about 30% by weight (or up to about 20% by weight or up to about 10% by weight or up to about 5% by weight), based on total weight of the mixture (e.g., about 0.1 to about 15% by weight).

It should be noted that inclusion of a tobacco material into the compositions and products described herein is meant to be optional and is not required. In some embodiments, oral products as described herein can generally be characterized as being tobacco free-alternatives. For example, in some embodiments, oral products of the present disclosure may be said to be completely free or substantially free of tobacco material (other than purified nicotine as an active ingredient). Oral products that are referred to as "completely free of" or "substantially free of" a tobacco material herein are meant to refer to oral products that can be characterized as having less than about 1.0% by weight, less than about 0.5% by weight, less than about 0.1% by weight of tobacco material, or 0% by weight of tobacco material.

Further Additives

In some embodiments, one or more further additives can be included in the material. For example, the compositions can be processed, blended, formulated, combined and/or mixed with other materials or ingredients. The additives can be artificial, or can be obtained or derived from herbal or biological sources. Specific types of further additives that may be included are further described below.

In some embodiments, the material may include a content of water. The water content of the composition within the product, prior to use by a consumer of the product, may vary according to the desired properties. Typically, the composition, as present within the product prior to insertion into the mouth of the user, can comprise less than 60%, less than 50%, less than 40%, less than 30%, less than 20%, less than 10%, or less than 5% by weight of water. For example, total water content in the composition and/or product may be in the range of about 0.1% to about 60%, about 1% to about 50%, about 1.5% to about 40%, or about 2% to about 25% by weight of water. In some embodiments, the compositions and products may include at least 1%, at least 2%, at least 5%, at least 10%, or at least 20% by weight water.

In some embodiments, the material may include a content of one or more organic acids. As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($—CO_2H$) or sulfonic acids ($—SO_2OH$). As used herein, reference to organic acid means an organic acid that is intentionally added. In this regard, an organic acid may be intentionally added as a specific ingredient as opposed to merely being inherently present as a component of another ingredient (e.g., the small amount of organic acid which may inherently be present in an ingredient such as a tobacco material). In some embodiments, the one or more organic acids are added neat (i.e., in their free acid, native solid or liquid form) or as a solution in, e.g., water. In some embodiments, the one or more organic acids are added in the form of a salt, as described herein below.

In some embodiments, the organic acid is an alkyl carboxylic acid. Non-limiting examples of alkyl carboxylic acids include formic acid, acetic acid, propionic acid, octanoic acid, nonanoic acid, decanoic acid, undecanoic acid, dodecanoic acid, stearic acid, oleic acid, linoleic acid, linolenic acid, and the like. In some embodiments, the organic acid is an alkyl sulfonic acid. Non-limiting examples of alkyl sulfonic acids include propanesulfonic acid and octanesulfonic acid. In some embodiments, the alkyl carboxylic or sulfonic acid is substituted with one or more hydroxyl groups. Non-limiting examples include glycolic acid, 4-hydroxybutyric acid, and lactic acid. In some embodiments, an organic acid may include more than one carboxylic acid group or more than one sulfonic acid group (e.g., two, three, or more carboxylic acid groups). Non-limiting examples include oxalic acid, fumaric acid, maleic acid, and glutaric acid. In organic acids containing multiple carboxylic acids (e.g., from two to four carboxylic acid groups), one or more of the carboxylic acid groups may be esterified. Non-limiting examples include succinic acid monoethyl ester, monomethyl fumarate, monomethyl or dimethyl citrate, and the like.

In some embodiments, the organic acid may include more than one carboxylic acid group and one or more hydroxyl groups. Non-limiting examples of such acids include tartaric acid, citric acid, and the like. In some embodiments, the organic acid is an aryl carboxylic acid or an aryl sulfonic acid. Non-limiting examples of aryl carboxylic and sulfonic acids include benzoic acid, toluic acids, salicylic acid, benzenesulfonic acid, and p-toluenesulfonic acid. In some embodiments, the organic acid is citric acid, malic acid, tartaric acid, octanoic acid, benzoic acid, a toluic acid, salicylic acid, or a combination thereof. In some embodiments, the organic acid is benzoic acid. In some embodiments, the organic acid is citric acid. In alternative embodiments, a portion, or even all, of the organic acid may be added in the form of a salt with an alkaline component, which may include, but is not limited to, nicotine. Non-limiting examples of suitable salts, e.g., for nicotine, include formate, acetate, propionate, isobutyrate, butyrate, alpha-methylbutyate, isovalerate, beta-methylvalerate, caproate, 2-furoate, phenylacetate, heptanoate, octanoate, nonanoate, oxalate, malonate, glycolate, benzoate, tartrate, levulinate, ascorbate, fumarate, citrate, malate, lactate, aspartate, salicylate, tosylate, succinate, pyruvate, and the like.

The amount of organic acid present in the compositions may vary. Generally, the compositions can comprise from 0 to about 10% by weight of organic acid, present as one or more organic acids, based on the total weight of the material.

In some embodiments, the material may further comprise a salt (e.g., alkali metal salts), typically employed in an amount sufficient to provide desired sensory attributes to the compositions and products. Non-limiting examples of suitable salts include sodium chloride, potassium chloride, ammonium chloride, flour salt, and the like. When present, a representative amount of salt is about 0.5 percent by weight or more, about 1.0 percent by weight or more, or at about 1.5 percent by weight or more, but will typically make up about 10 percent or less of the total weight of the composition or product, or about 7.5 percent or less or about 5 percent or less (e.g., about 0.5 to about 5 percent by weight).

The material also may include one or more sweeteners. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, isomaltulose, stevia, honey, and the like. Examples of artificial sweeteners include sucralose, maltodextrin, saccharin, aspartame, acesulfame K, neotame and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). When present, a representative amount of sweetener may make up from about 0.1 to about 20 percent or more of the of the composition by weight, for example, from about 0.1 to about 1%, from about 1 to about 5%, from about 5 to about 10%, or from about 10 to about 20% of the material on a weight basis, based on the total weight of the material.

In some embodiments, the material may include one or more binding agents. A binder (or combination of binders) may be employed in certain embodiments, in amounts sufficient to provide the desired physical attributes and physical integrity to the composition, and binders also often function as thickening or gelling agents. Typical binders can be organic or inorganic, or a combination thereof. Representative binders include povidone, sodium alginate, starch-based binders, pectin, carrageenan, pullulan, zein, and the like, and combinations thereof. In some embodiments, the binder comprises pectin or carrageenan or combinations thereof. The amount of binder utilized can vary, but is typically up to about 30 weight percent, and certain embodiments are characterized by a binder content of at least about 0.1% by weight, such as about 1 to about 30% by weight, or about 5 to about 10% by weight, based on the total weight of the material.

In certain embodiments, the binder includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the material.

In certain embodiments, one or more humectants may be employed in the mixture. Examples of humectants include, but are not limited to, glycerin, propylene glycol, and the like. Where included, the humectant is typically provided in an amount sufficient to provide desired moisture attributes to the compositions. Further, in some instances, the humectant may impart desirable flow characteristics to the composition for depositing in a mold. When present, a humectant will typically make up about 5% or less of the weight of the material (e.g., from about 0.5 to about 5% by weight). When present, a representative amount of humectant is about 0.1% to about 1% by weight, or about 1% to about 5% by weight, based on the total weight of the material.

In certain embodiments, the materials of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Where present, the buffering agent is typically present in an amount less than about 5 percent based on the weight of the material, for example, from about 0.5% to about 5%, such as, e.g., from about 0.75% to about 4%, from about 0.75% to about 3%, or from about 1% to about 2% by weight, based on the total weight of the substrate material. Non-limiting examples of suitable buffers include alkali metals acetates, glycinates, phosphates, glycerophosphates, citrates, carbonates, hydrogen carbonates, borates, or mixtures thereof.

In some embodiments, the material may include one or more colorants. A colorant may be employed in amounts sufficient to provide the desired physical attributes to the composition or product. Examples of colorants include various dyes and pigments, such as caramel coloring and titanium dioxide. The amount of colorant utilized in the compositions or products can vary, but when present is typically up to about 3 weight percent, such as from about 0.1%, about 0.5%, or about 1%, to about 3% by weight, based on the total weight of the material.

Examples of even further types of additives that may be used in the present materials include thickening or gelling agents (e.g., fish gelatin), emulsifiers, oral care additives (e.g., thyme oil, eucalyptus oil, and zinc), preservatives (e.g., potassium sorbate and the like), disintegration aids, zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final mixture, with an example range of up to about 10% by weight, based on total weight of the substrate material (e.g., about 0.1 to about 5% by weight).

The aforementioned additives can be employed together (e.g., as additive formulations) or separately (e.g., individual additive components can be added at different stages involved in the preparation of the final substrate material). Furthermore, the aforementioned types of additives may be encapsulated as provided in the final product or material to be included within the final product. Example encapsulated additives are described, for example, in WO2010/132444 to Atchley, which has been previously incorporated by reference herein.

Particles

In some embodiments, any one or more of a filler, a tobacco material, and the overall substrate material described herein can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 µm, such as 500 µm, such as 400 µm, such as 300 µm.

In some embodiments, any particulate material referenced herein (e.g., filler component, tobacco material, and the overall substrate material) can be characterized as having at least 50% by weight of particles with a particle size as measured by sieve analysis of no greater than about 1000 µm, such as no greater than about 500 µm, such as no greater than about 400 µm, such as no greater than about 350 µm, such as no greater than about 300 µm. In some embodiments, at least 60% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 70% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 80% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 90% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 95% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 99% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, approximately 100% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 µm to about 1000 µm, such as from about 0.05 µm to about 750 µm, such as from about 0.1 µm to about 500 µm, such as from about 0.25 µm to about 500 µm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 µm to about 400 µm, such as from about 50 µm to about 350 µm, such as from about 100 µm to about 350 µm, such as from about 200 µm to about 300 µm.

Preparation of the Material for Inclusion within the Pouch

The manner by which the various components of the material are combined may vary. As such, the overall mixture of various components with e.g., powdered mixture components may be relatively uniform in nature. The components noted above, which may be in liquid or dry solid form, can be admixed in a pretreatment step prior to mixture with any remaining components of the material, or simply mixed together with all other liquid or dry ingredients. The various components of the material may be contacted, combined, or mixed together using any mixing technique or equipment known in the art. Any mixing method that brings the ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components forming the material are prepared such that the mixture thereof may be used in a starch molding process for forming the mixture. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

The amount of material contained within each product unit, for example, a pouch, may vary. In some embodiments, the weight of the mixture within each pouch is at least about 50 mg, for example, from about 50 mg to about 2 grams, from about 100 mg to about 1.5 grams, or from about 200 to about 700 mg. In some smaller embodiments, the weight of the mixture within each pouch may be from about 100 to about 300 mg. For a larger embodiment, the weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and U.S. Pat. No. 6,923,981 to Leung et al.; and The EFSA Journal (2004) 85, 1-32; which are incorporated herein by reference.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An oral pouched product, comprising a material within a porous pouch, wherein the porous pouch comprises a fleece material having a basis weight of at least about 35 gsm and a density of at least about 4 g/cc.

2. The oral pouched product of claim 1, wherein the fleece material has a basis weight of about 35 gsm to about 40 gsm.

3. The oral pouched product of claim 1, wherein the fleece material has a thickness of at least about 0.2 mm.

4. The oral pouched product of claim 1, wherein the fleece material has a thickness of less than about 0.1 mm.

5. The oral pouched product of claim 1, wherein the fleece material has a density of about 5 g/cc to about 7.5 g/cc.

6. The oral pouched product of claim 1, wherein the fleece material has a density of about 4 g/cc to about 8 g/cc.

7. The oral pouched product of claim 1, wherein the fleece material further comprises a binder.

8. The oral pouched product of claim 1, wherein the material comprises an active ingredient.

9. The oral pouched product of claim 8, wherein the active ingredient is selected from the group consisting of a nicotine component, botanicals, nutraceuticals, stimulants, amino acids, vitamins, cannabinoids, cannabimimetics, terpenes, and combinations thereof.

10. The oral pouched product of claim 1, wherein the material comprises one or more additives selected from the group consisting of a flavoring agent, a salt, a sweetener, a binding agent, water, a humectant, a gum, an organic acid, a buffering agent and/or a pH adjuster, a tobacco material, and combinations thereof.

11. The oral pouched product of claim 1, wherein the oral pouched product is substantially free of a tobacco material.

* * * * *